United States Patent
Kotani et al.

(10) Patent No.: US 7,279,293 B2
(45) Date of Patent: Oct. 9, 2007

(54) CONSTITUTIVELY ACTIVE HISTAMINE H3 RECEPTOR MUTANTS AND USES THEREOF

(75) Inventors: Hidehito Kotani, Ibaraki (JP); Kazuhiko Takahashi, Ibaraki (JP); Shigeru Tokita, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 98 days.

(21) Appl. No.: 10/512,240

(22) PCT Filed: Apr. 23, 2003

(86) PCT No.: PCT/JP03/05184

§ 371 (c)(1),
(2), (4) Date: Jun. 8, 2005

(87) PCT Pub. No.: WO03/091282

PCT Pub. Date: Nov. 6, 2003

(65) Prior Publication Data

US 2005/0234223 A1    Oct. 20, 2005

(30) Foreign Application Priority Data

Apr. 24, 2002 (JP) ............................. 2002-123005

(51) Int. Cl.
*C07K 14/705* (2006.01)
*C07K 19/00* (2006.01)
*G01N 33/566* (2006.01)
*C12N 15/62* (2006.01)

(52) U.S. Cl. .................... 435/7.21; 435/69.7; 530/530; 536/23.4

(58) Field of Classification Search ............... 435/7.21, 435/69.7; 530/350; 536/23.4
See application file for complete search history.

(56) References Cited

U.S. PATENT DOCUMENTS

| | | | |
|---|---|---|---|
| 4,767,778 A | 8/1988 | Arrang et al. | |
| 5,194,596 A | 3/1993 | Tischer et al. | |
| 5,342,960 A | 8/1994 | Garbarg et al. | |
| 5,882,893 A | 3/1999 | Goodearl | |
| 6,093,545 A | 7/2000 | Goodearl et al. | 435/6 |
| 6,750,322 B2 | 6/2004 | Itadani et al. | |
| 7,074,594 B2 | 7/2006 | Itadani et al. | |
| 2007/0015220 A1 | 1/2007 | Itadani et al. | |

FOREIGN PATENT DOCUMENTS

| | | |
|---|---|---|
| WO | WO 91/17146 | 11/1991 |
| WO | WO 99/28470 | 6/1999 |
| WO | WO 99/33978 | 7/1999 |
| WO | WO 00/20011 | 4/2000 |
| WO | WO 00/39164 | 7/2000 |
| WO | WO 01/68816 | 7/2001 |
| WO | WO 01/77172 | 10/2001 |
| WO | WO 03/004637 | 1/2003 |
| WO | WO 03/091282 | 11/2003 |

OTHER PUBLICATIONS

Ligneau et al. Distinct Pharmacology of Rat and Human Histamine H3 Receptors: Role of Two Amino Acids in the Third Transmembrane Domain. 2000, British Journal of Pharmacology 131:1247-1250.*

Kjelsberg MA et al., "Constitutive activation of the alpha 1B-adrenergic receptor by all amino acid substitutions at a single site. Evidence for a region which constrains receptor activation." J. Biol. Chem., vol. 267(3), pp. 1430-1433 (1992).

Costa T. et al., "Drug Efficacy at Guanine Nucleotide-Binding Regulatory Protein-Linked Receptors: Thermodynamic Interpretation of Negative Antagonism and of Receptor Activity in the Absence of Ligand", Mol. Pharmacol, vol. 41(3), pp. 549-560 (1992).

Lefkowitz RJ et al., "Constitutive activity of receptors coupled to guanine nucleotide regulatory proteins", Trends Pharmacol Sci, vol. 14(8), pp. 303-307 (1993).

Milligan G. et al., "Inverse agonism: pharmacological curiosity of potential therapeutic strategy?", Trends Pharmacol Sci, vol. 16(1), pp. 10-13 (1995).

Lovenberg TW et al., "Cloning and Functional Expression of the Human Histamine $H_3$ Receptor", Mol Pharmacol, vol. 55(6), pp. 1101-1107 (1999).

Lovenberg TW et al., "Cloning of Rat Histamine $H_3$ Receptor Reveals Distinct Species Pharmacological Profiles", J. Pharmacol Exp Ther, vol. 293(3), pp. 771-778 (2000).

Tarvidel-Lacombe J. et al., "Cloning and cerebral expression of the guinea pig histamine $H_3$ receptor: evidence for two isoforms", Neuroreport, vol. 11(4), pp. 755-759 (2000).

Morisset S. et al., "High constitutive activity of native $H_3$ receptors regulates histamine neurons in brain", Nature, vol. 408(6814), pp. 860-864 (2000).

Francesconi A. et al., "Role of the Second and Third Intracellular Loops of Metabotropic Glutamate Receptors in Mediating Dual Signal Transduction Activation", J Biol Chem, vol. 273(10), pp. 5615-5624 (1998).

Hasegawa H. et al., "Two Isoforms of the Prostaglandin E Receptor EP3 Subtype Different in Agonist-independent Constitutive Activity", J Biol Chem, vol. 271(4), pp. 1857-1860(1996).

Leurs R. et al., "Therapeutic potential of histamine $H_3$ receptor agonists and antagonists", Trends Pharmacol Sci, vol. 19(5), pp. 177-183 (1998).

Onodera K. et al., Nihon Shinkei Seishin Yakurigaku Zasshi, vol. 15(2), pp. 87-102 (1995).

(Continued)

*Primary Examiner*—John Ulm
(74) *Attorney, Agent, or Firm*—Fish & Richardson P.C.

(57) ABSTRACT

Internal domain 3 of seven transmembrane G protein-coupled receptors is important for G protein binding or receptor activity, and is well conserved. In H3 receptors, which are a type of G protein-coupled receptor, this region is also conserved in the same way. Therefore, as a result of using PCR to introduce point mutations into sequences encoding the region in H3 receptor cDNA, H3 receptor mutants comprising extremely strong constitutive activity could be successfully produced. The present inventors further found that by using constitutively active H3 receptor mutants, drug candidate compounds such as H3 receptor inverse agonists can be screened more easily and efficiently.

21 Claims, 5 Drawing Sheets

OTHER PUBLICATIONS

Rouleau A. et al., "Histamine H3-receptor-mediated [$^{35}$S]GTPγ[S] binding: evidence for constitutive activity of the recombinant and native rat and human H$_3$ receptors", British Journal of Pharmacology, vol. 135, pp. 383-392 (2002).

Wieland K. et al., "Constitutive Activity of Histamine H$_3$ Receptors Stably Expressed in SK-N-MC Cells: Display of Agonism and Inverse Agonism by H$_3$ Antagonists", The Journal of Pharmacology and Experimental Therapeutics, vol. 299(3), pp. 908-914 (2001).

Adachi et al., "Cloning and Characterization of cDNA Encoding Human A-Type Endothelin Receptor," *Biochem. Biophys. Res. Commun.*, 180:1265-1272 (1991).

Arrang et al., "Auto-inhibition of brain histamine release mediated by a novel class (H$_3$)of histamine receptor," *Nature*, 302:832-837 (1983).

Arrang et al., "Highly potent and selective ligands for histamine H$_3$-receptors," *Nature*, 327:117-123 (1987).

Benjamin et al., "A plasticity window for blood vessel remodelling is defined by pericyte coverage of the preformed endothelial network and is regulated by PDGF-B and VEGF," *Development*, 125:1591-1598 (1988).

Bonner et al., "Cloning and Expression of the Human and Rat m5 Muscarinic Acetylcholine Receptor Genes," *Neuron*, 1:403-410 (1988).

Bork, "Powers and Pitfalls in Sequence Analysis: The 70% Hurdle," *Genome Res.*, 10:398-400, (2000).

Bruno et al., "Molecular Cloning and Sequencing of a cDNA Encoding a Human α$_{1A}$ Adrenergic Receptor," *Biochem. Biophys. Res. Commun.*, 179:1485-1490 (1991).

Cherifi et al., "Purification of a Histamine H$_3$ Receptor Negatively Coupled to Phosphoinositide Turnover in the Human Gastric Cell Line HGT1," *J. Biol. Chem.*, 267:25315-25320 (1992).

EMBL Accession No. AA859887, 2 pages (Mar. 14, 1998).

Frielle et al., "Cloning of the cDNA for the human β$_{1\text{-adrenergic receptor}}$," *Proc. Natl. Acad. Sci. USA*, 84:7920-7924 (1987).

GenBank Accession No. R87217, 1 page (Oct. 10, 1995).

Jasper et al., "Primary structure of the mouse β$_1$-adrenergic receptor gene," *Biochim. Biophys. Acta*, 1178:307-309 (1993).

Kakar et al., "Cloning, Sequencing, and Expression of Human Gonadotropin Releasing Hormone (GnRH) Receptor," *Biochem. Biophys. Res. Commun.*, 189:289-295 (1992).

Laitinen et al., "Guanosine 5'-(γ-[$^{35}$S]Thio)triphosphate Autoradiography Allows Selective Detection of Histamine H$_3$ Receptor-Dependent G Protein Activation in Rat Brain Tissue Sections," *J. Neurochem.*, 71:808-816 (1998).

Lameh et al., "Structure and Function of G Protein Coupled Receptors," *Pharm. Res.*, 7:1213-1221 (1990).

Larhammar et al., "Cloning and Functional Expression of a Human Neuropeptide Y/Peptide YY Receptor of the Y1 Type," *J. Biol. Chem.*, 267:10935-10938 (1992).

Lee et al., "Cloning and expression of a cDNA encoding bovine muscarinic acetylcholine m3 receptor," *Biochim. Biophys. Acta*, 1223:151-154 (1994).

Leurs et al., "The histamine H$_3$receptor: A target for developing new drugs," *Prog. Drug Res.*, 39:127-165 (1992).

Libert et al., "Selective Amplification and Cloning of Four New Members of the G Protein-Coupled Receptor Family," *Science*, 244:569-572 (1989).

Link et al., "Cloning of Two Mouse Genes Encoding α$_2$-Adrenergic Receptor Subtypes and Identification of a Single Amino Acid in the Mouse α$_2$-C10 Homolog Responsible for an Interspecies Variation in Antagonist Binding," *Mol. Pharmacol.*, 42:16-27 (1992).

Mahan et al., "Expression of striatal D$_1$ dopamine receptors coupled to inositol phosphate production and Ca$^{2+}$mobilization in *Xenopus* oocytes," *Proc. Natl. Acad. Sci. USA*, 87:2196-2200 (1990).

Masu et al., "Sequence and expression of a metabotropic glutamate receptor," *Nature*, 349:760-765 (1991).

Peralta et al., "Distinct primary structures, ligand-binding properties and tissue-specific expression of four human muscarinic acetylcholine receptors," *EMBO J.*, 6:3923-3929 (1987).

Regan et al., "Cloning and expression of a human kidney cDNA for an α2-adrenergic receptor subtype," *Proc. Natl. Acad. Sci. USA*, 85:6301-6305 (1988).

Ruat et al., "Reversible and irreversible labeling and autoradiographic localization of the cerebral histamine H$_2$ receptor using [$^{125}$I]iodinated probes," *Proc. Natl. Acad. Sci. USA*, 87:1658-1662 (1990).

Segal et al., "*Helicobacter pylori* attachment to gastric cells induces cytoskeletal rearrangements and tyrosine phosphorylation of host cell proteins," *Proc. Natl. Acad. Sci. USA*, 93:1259-1264 (1996).

Skolnick et al., "From genes to protein structure and function: novel applications of computational approaches in the genomic era," *Trends Biotechnol.*, 18:34-39 (2000).

Takayanagi et al., "Molecular Cloning, Sequence Analysis and Expression of a cDNA Encoding Human Type-1 Angiotensin II Receptor," Biochem. Biophys. Res. Commun., 183;910-916 (1992).

Wells, "Additivity of Mutational Effects in Proteins," *Biochemistry*, 29:8509-8517 (1990).

Yamada et al., "Cloning and functional characterization of a family of human and mouse somatostatin receptors expressed in brain, gastrointestinal tract, and kidney," *Proc. Natl. Acad. Sci. USA*, 89:251-255 (1992).

* cited by examiner

|       |    | R   | D   | K   | K   | V   | A   | K   | S   |       |                |
|-------|----|-----|-----|-----|-----|-----|-----|-----|-----|-------|----------------|
| m-H3  | 5'-| CGG | GAC | AAG | AAG | GTA | GCC | AAG | TCG | -3'   | (SEQ ID NO:13) |
| MT1   | 5'-| CGG | GAC | AAG | AAG | GTA | CTC | AAG | TCG | -3'   | (SEQ ID NO:14) |
| MT2   | 5'-| AAG | GAC | CAC | AAG | GTA | CTC | AAG | TCG | -3'   | (SEQ ID NO:15) |
| MT3   | 5'-| CGG | GCC | AAG | AAG | GTA | GCC | AAG | TCG | -3'   | (SEQ ID NO:16) |
| MT5   | 5'-| CGG | GAC | AAG | AAG | GTA | ATC | AAG | TCG | -3'   | (SEQ ID NO:17) |
| MT6   | 5'-| CGG | GAC | AAG | AAG | GTA | AAG | AAG | TCG | -3'   | (SEQ ID NO:18) |

FIG. 1

```
        351              360
m-H3   S R D K K V A K S L   (SEQ ID NO : 27)
MT1    S R D K K V[L]K S L   (SEQ ID NO : 28)
MT2    S[K]D[H]K V[L]K S L   (SEQ ID NO : 29)
MT3    S R[A]K K V A K S L   (SEQ ID NO : 30)
MT5    S R D K K V[I]K S L   (SEQ ID NO : 31)
MT6    S R D K K V[K]K S L   (SEQ ID NO : 32)
```

FIG. 2

```
              351              360
h-H3    S R D R K V A K S L    (SEQ ID NO : 33 )
MT1     S R D R K V[L]K S L    (SEQ ID NO : 34 )
MT2     S[K]D[H]K V[L]K S L    (SEQ ID NO : 35 )
MT3     S R[A]R K V A K S L    (SEQ ID NO : 36 )
MT5     S R D R K V[I]K S L    (SEQ ID NO : 37 )
MT6     S R D R K V[K]K S L    (SEQ ID NO : 38 )
```

FIG. 3

SEQUENCE LISTING

```
<160> NUMBER OF SEQ ID NOS: 38

<210> SEQ ID NO 1
<211> LENGTH: 445
<212> TYPE: PRT
<213> ORGANISM: Mus musculus

<400> SEQUENCE: 1

Met Glu Arg Ala Pro Pro Asp Gly Leu Met Asn Ala Ser Gly Ala Leu
  1               5                  10                  15

Ala Gly Glu Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
         35                  40                  45

Val Leu Gly Asn Ala Leu Val Met Leu Ala Phe Val Ala Asp Ser Ser
     50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
```

```
                        85                  90                  95
Thr Gly Arg Trp Thr Phe Gly Arg Gly Leu Cys Lys Leu Trp Leu Val
                100                 105                 110
Val Asp Tyr Leu Leu Cys Ala Ser Ser Val Phe Asn Ile Val Leu Ile
            115                 120                 125
Ser Tyr Asp Arg Phe Leu Ser Val Thr Arg Ala Val Ser Tyr Arg Ala
        130                 135                 140
Gln Gln Gly Asp Thr Arg Arg Ala Val Arg Lys Met Ala Leu Val Trp
145                 150                 155                 160
Val Leu Ala Phe Leu Leu Tyr Gly Pro Ala Ile Leu Ser Trp Glu Tyr
                165                 170                 175
Leu Ser Gly Gly Ser Ser Ile Pro Glu Gly His Cys Tyr Ala Glu Phe
                180                 185                 190
Phe Tyr Asn Trp Tyr Phe Leu Ile Thr Ala Ser Thr Leu Glu Phe Phe
            195                 200                 205
Thr Pro Phe Leu Ser Val Thr Phe Phe Asn Leu Ser Ile Tyr Leu Asn
        210                 215                 220
Ile Gln Arg Arg Thr Arg Leu Arg Leu Asp Gly Gly Arg Glu Ala Gly
225                 230                 235                 240
Pro Glu Pro Pro Asp Ala Gln Pro Ser Pro Pro Ala Pro Pro
                245                 250                 255
Ser Cys Trp Gly Cys Trp Pro Lys Gly His Gly Glu Ala Met Pro Leu
                260                 265                 270
His Arg Tyr Gly Val Gly Glu Ala Gly Pro Gly Val Glu Thr Gly Glu
                275                 280                 285
Ala Gly Leu Gly Gly Gly Ser Gly Gly Ala Ala Ala Ser Pro Thr
        290                 295                 300
Ser Ser Ser Gly Ser Ser Ser Arg Gly Thr Glu Arg Pro Arg Ser Leu
305                 310                 315                 320
Lys Arg Gly Ser Lys Pro Ser Ala Ser Ala Ser Leu Glu Lys Arg
                325                 330                 335
Met Lys Met Val Ser Gln Ser Ile Thr Gln Arg Phe Arg Leu Ser Arg
                340                 345                 350
Asp Lys Lys Val Ala Lys Ser Leu Ala Ile Ile Val Ser Ile Phe Gly
            355                 360                 365
Leu Cys Trp Ala Pro Tyr Thr Leu Leu Met Ile Ile Arg Ala Ala Cys
        370                 375                 380
His Gly His Cys Val Pro Asp Tyr Trp Tyr Glu Thr Ser Phe Trp Leu
385                 390                 395                 400
Leu Trp Ala Asn Ser Ala Val Asn Pro Val Leu Tyr Pro Leu Cys His
                405                 410                 415
Tyr Ser Phe Arg Arg Ala Phe Thr Lys Leu Leu Cys Pro Gln Lys Leu
                420                 425                 430
Lys Val Gln Pro His Gly Ser Leu Glu Gln Cys Trp Lys
        435                 440                 445

<210> SEQ ID NO 2
<211> LENGTH: 1338
<212> TYPE: DNA
<213> ORGANISM: Mus musculus

<400> SEQUENCE: 2
atggagcgcg cgccgcccga cgggctgatg aacgcgtcgg gcgctctggc cggagaggcg    60
gcggctgcag gcggggcgcg cggcttctcg gctgcctgga ccgctgtcct ggctgcgctc   120
```

```
atggcgctgc tcatcgtggc cacagtgctg ggcaacgcgc tggtcatgct cgccttcgtg      180
gcggattcga gcctccgcac ccagaacaac ttctttctgc tcaacctcgc catctccgac      240
ttcctcgtgg gtgccttctg catcccattg tatgtaccct atgtgctgac cggccgttgg      300
acctttggcc ggggcctctg caagctgtgg ctggtggtag actacctact gtgtgcctcc      360
tcagtcttca acatcgtgct gatcagctat gaccgattcc tgtcagtcac tcgagctgtc      420
tcctacaggg cccagcaggg ggacacaaga cgggctgttc ggaagatggc actggtgtgg      480
gtgctggcct tcctgctgta tgggcctgcc atcctgagtt gggagtacct gtccggtggc      540
agctccatcc ccgagggcca ctgctatgct gagttcttct acaactggta ctttctcatc      600
acggcctcca ccctcgagtt cttcacaccc ttcctcagcg ttaccttctt caacctcagc      660
atctacctga acatccagag gcgcactcgt cttcggctgg atgggggccg agaggctggt      720
ccagaacccc cacctgatgc ccaaccctcg ccacctccag ctcccccag ctgctggggc      780 tgctggccaa aggggcacgg ggaggccatg ccattgcaca ggtatggggt gggtgaggca      840
ggccctggtg ttgagactgg ggaggctggc ctcgggggtg gcagcggtgg aggcgctgct      900
gcctcgccta cctccagctc cggcagctcc tcaaggggca ctgagaggcc acgctcactc      960
aaaaggggct ccaagccatc agcgtcttca gcgtccttgg agaagcgcat gaagatggta     1020
tcccaaagca tcacccagcg ctttcggctg tcgcgggaca gaaggtagc caagtcgctg     1080 gctatcatcg tgagcatctt tgggctctgc tgggccccgt acacactcc catgatcatc     1140 cgggctgctt gccatggcca ctgcgtcccc gactactggc acgagacgtc cttctggctt     1200
ctgtgggcca actcggccgt caaccccgtc ctctacccac tgtgccacta cagcttccgt     1260
agagccttca ccaagctcct ctgccccag aagctcaagg tccagcccca tggctccctg     1320
gagcagtgct ggaagtga                                                   1338
```

<210> SEQ ID NO 3
<211> LENGTH: 445
<212> TYPE: PRT
<213> ORGANISM: Homo sapiens

<400> SEQUENCE: 3

```
Met Glu Arg Ala Pro Pro Asp Gly Pro Leu Asn Ala Ser Gly Ala Leu
  1               5                  10                  15

Ala Gly Glu Ala Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
         35                  40                  45

Val Leu Gly Asn Ala Leu Val Met Leu Ala Phe Val Ala Asp Ser Ser
     50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
                 85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Leu Leu Val Trp
```

```
                145                 150                 155                 160
Val Leu Ala Phe Leu Leu Tyr Gly Pro Ala Ile Leu Ser Trp Glu Tyr
                    165                 170                 175

Leu Ser Gly Gly Ser Ser Ile Pro Glu Gly His Cys Tyr Ala Glu Phe
                    180                 185                 190

Phe Tyr Asn Trp Tyr Phe Leu Ile Thr Ala Ser Thr Leu Glu Phe Phe
                    195                 200                 205

Thr Pro Phe Leu Ser Val Thr Phe Phe Asn Leu Ser Ile Tyr Leu Asn
                    210                 215                 220

Ile Gln Arg Arg Thr Arg Leu Arg Leu Asp Gly Ala Arg Glu Ala Ala
225                 230                 235                 240

Gly Pro Glu Pro Pro Glu Ala Gln Pro Ser Pro Pro Pro Pro
                    245                 250                 255

Gly Cys Trp Gly Cys Trp Gln Lys Gly His Gly Glu Ala Met Pro Leu
                    260                 265                 270

His Arg Tyr Gly Val Gly Glu Ala Val Gly Ala Glu Ala Gly Glu
                    275                 280                 285

Ala Thr Leu Gly Gly Gly Gly Gly Ser Val Ala Ser Pro Thr
290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                    325                 330                 335

Met Lys Met Val Ser Gln Ser Phe Thr Gln Arg Phe Arg Leu Ser Arg
                    340                 345                 350

Asp Arg Lys Val Ala Lys Ser Leu Ala Val Ile Val Ser Ile Phe Gly
                    355                 360                 365

Leu Cys Trp Ala Pro Tyr Thr Leu Leu Met Ile Ile Arg Ala Ala Cys
            370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                    405                 410                 415

His Ser Phe Arg Arg Ala Phe Thr Lys Leu Leu Cys Pro Gln Lys Leu
                    420                 425                 430

Lys Ile Gln Pro His Ser Ser Leu Glu His Cys Trp Lys
            435                 440                 445

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 4

Lys Asp His Lys Val Leu Lys
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence
```

```
<400> SEQUENCE: 5

Arg Ala Arg Lys Val Ala Lys
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 6

Arg Asp Arg Lys Val Ile Lys
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 7

Arg Asp Arg Lys Val Lys Lys
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 8

Arg Ala Lys Lys Val Ala Lys
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 9

Arg Asp Lys Lys Val Ile Lys
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 10

Arg Asp Lys Lys Val Lys Lys
  1               5

<210> SEQ ID NO 11
<211> LENGTH: 7
<212> TYPE: PRT
```

```
<213> ORGANISM: Artificial Sequence
<220> FEATURE:
<223> OTHER INFORMATION: Description of Artificial Sequence: Consensus
      Sequence

<400> SEQUENCE: 11

Arg Asp Arg Lys Val Ala Lys
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Consensus
      Sequence

<400> SEQUENCE: 12

Arg Asp Lys Lys Val Ala Lys
  1               5

<210> SEQ ID NO 13
<211> LENGTH: 24
<212> TYPE: DNA
<213> ORGANISM: Mus musculus

<400> SEQUENCE: 13
cgggacaaga aggtagccaa gtcg                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: An
      Artificially Synthesized Nucleotide Sequence

<400> SEQUENCE: 14
cgggacaaga aggtactcaa gtcg                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: An
      Artificially Synthesized Nucleotide Sequence

<400> SEQUENCE: 15
aaggaccaca aggtactcaa gtcg                                          24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: An
      Artificially Synthesized Nucleotide Sequence

<400> SEQUENCE: 16
cgggccaaga aggtagccaa gtcg                                          24

<210> SEQ ID NO 17
<211> LENGTH: 24
<212> TYPE: DNA
<213> ORGANISM: Artificial Sequence
<220> FEATURE:
```

```
<223> OTHER INFORMATION: Description of Artificial Sequence: An
      Artificially Synthesized Nucleotide Sequence

<400> SEQUENCE: 17
cgggacaaga aggtaatcaa gtcg                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: An
      Artificially Synthesized Nucleotide Sequence

<400> SEQUENCE: 18
cgggacaaga aggtaaagaa gtcg                                              24

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 19
agaaccccca cctgatgc                                                     18

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 20
tcacttccag cactgctcca gg                                                22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 21
gcactcgtct tcggctggat g                                                 21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 22
cgacttgagt accttcttgt c                                                 21

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: An
```

-continued

Artificially Synthesized Primer Sequence

<400> SEQUENCE: 23
cgacttgagt accttgtggt ccttcgacag ccg                                33

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 24
cttcttggcc cgcgacagcc g                                             21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 25
cgacttgatt accttcttgt c                                             21

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: An
      Artificially Synthesized Primer Sequence

<400> SEQUENCE: 26
cgacttcttt accttcttgt cccg                                          24

<210> SEQ ID NO 27
<211> LENGTH: 10
<212> TYPE: PRT
<213> ORGANISM: Mus musculus

<400> SEQUENCE: 27

Ser Arg Asp Lys Lys Val Ala Lys Ser Leu
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 28

Ser Arg Asp Lys Lys Val Leu Lys Ser Leu
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

```
<400> SEQUENCE: 29

Ser Lys Asp His Lys Val Leu Lys Ser Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 30

Ser Arg Ala Lys Lys Val Leu Lys Ser Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 31

Ser Arg Asp Lys Lys Val Ile Lys Ser Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 32

Ser Arg Asp Lys Lys Val Lys Lys Ser Leu
1               5                   10

<210> SEQ ID NO 33
<211> LENGTH: 10
<212> TYPE: PRT
<213> ORGANISM: Homo sapiens

<400> SEQUENCE: 33

Ser Arg Asp Arg Lys Val Ala Lys Ser Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 34

Ser Arg Asp Arg Lys Val Leu Lys Ser Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: An
```

-continued

```
Artificially Synthesized Peptide Sequence

<400> SEQUENCE: 35

Ser Lys Asp His Lys Val Leu Lys Ser Leu
  1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 36

Ser Arg Ala Arg Lys Val Leu Lys Ser Leu
  1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 37

Ser Arg Asp Arg Lys Val Ile Lys Ser Leu
  1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: An
      Artificially Synthesized Peptide Sequence

<400> SEQUENCE: 38

Ser Arg Asp Arg Lys Val Lys Lys Ser Leu
  1               5                  10
```

CONSTITUTIVELY ACTIVE HISTAMINE H3 RECEPTOR MUTANTS AND USES THEREOF

TECHNICAL FIELD

The present invention relates to constitutively active histamine H3 receptor mutants and uses thereof.

BACKGROUND ART

Many hormones and neurotransmitters regulate body functions through specific receptors present on the cell membrane. Many of these receptors transmit signals into cells by activating conjugating guanosine triphosphate-binding proteins (G proteins). These receptors are therefore generically referred to as G protein-coupled receptors (GPCRs). Alternatively, since they also share a structure comprising a seven membrane-permeating region, they are also generically referred to as 'seven transmembrane' receptors.

G protein-coupled receptors are present on various functional cell surfaces in cells and organs of the body, and play extremely important roles as targets of molecules such as, for example, hormones, neurotransmitters, and physiologically active substances that regulate the functions of these cells and organs of the body. Consequently, G protein-coupled receptors have been attracting considerable attention as targets of drug development. A number of G protein-coupled receptors are known to be constitutively active (Costa, T. et al., Mol Pharmacol, 41, 549-560, 1992; Lefkowitz, R. et al., Trends Pharmaco. Sci., 14, 303-307, 1993). In some cases when a mutation is introduced into G protein-coupled receptors, their activity is known to further increase. For example, a constitutively active mutant of the a1B-adrenaline receptor, a type of G protein-coupled receptor, is known (Kjelsberg, M. A. et al., J. Biol. Chem. 267, 1430-33, 1992). Additionally, WO 01/77172 discloses constitutively active mutants of various G protein-coupled receptors.

In addition, antagonists that exhibit actions opposite to agonist have recently been discovered, indicating that the inverse agonists may be drug candidate compounds targeting G protein-coupled receptors (Milligan, G. et al., Trends Pharmaco. Sci., 16, 10-13, 1995). When inverse agonists act on G protein-coupled receptors, a conformation change arises, which is thought to increase the proportion of inactive forms (Milligan, G. et al., Trends Pharmaco. Sci., 16, 10-13, 1995).

Histamine H3 receptors (H3 receptors) are known to be a type of G protein-coupled receptor. Genes that encode these receptors are reported to exist in various living organisms, such as humans (Lovenberg, T. W. et al., Molecular Pharmacology, 55: 1101-1107, 1999; Lovenberg, T. W. et al., Journal of Pharmacology and Experimental Therapeutics, 293: 771-778, 2000; Tardivel-Lacombe, J. et al., Molecular Neuroscience, 11: 755-759, 2000; WO 2003004637). H3 receptor gene knockout mice have been found to demonstrate increased body weight, food intake and blood insulin or blood leptin levels, thus clearly indicating a correlation between H3 receptors and diseases characterized by changes in body weight, food intake and blood insulin or blood leptin levels (WO 2003004637). Furthermore, H3 receptors are constitutively active, even in their natural states, and have been reported to easily adopt constitutively active conformations (Morisset, S. et al., Nature, 408, 860-864, 2000). However, to date there have been no reports of examples of constitutively active H3 receptor mutants.

DISCLOSURE OF THE INVENTION

In consideration of the aforementioned circumstances, the object of the present invention is to produce constitutively active H3 receptor mutants, and to provide methods of screening for drug candidate compounds using these constitutively active mutants.

The present inventors conducted extensive research to solve the aforementioned problems. Internal domain 3 of the seven transmembrane G protein-coupled receptors is important for G protein binding or receptor activity, and is well conserved. In H3 receptors, which are a type of G protein-coupled receptor, this region is also conserved in the same way. Therefore, an attempt was made to produce constitutively active H3 receptor mutants. First, PCR was used to introduce point mutations into sequences that encode this conserved region in mouse H3 receptor cDNA, thus producing clones MT1, MT2, MT3, MT5, and MT6. Next, wild type mouse H3 receptor cDNA and five mouse H3 receptor mutant cDNAs were respectively transfected into cell line HEK293. cAMP levels were then measured using ELISA. As a result, cAMP levels in all clones were found to decrease in a histamine dose-dependent manner in the presence of 10 µM forskolin. In addition, cAMP levels were found to increase with increased doses of thioperamide, an H3 inverse agonist, in the presence of 10 µM forskolin. Moreover, with the exception of the MT1 clone, cAMP levels were found to be increased compared to natural H3 receptors. The above results indicate that the present inventors had succeeded in producing H3 receptor mutants comprising extremely strong constitutive activity. In addition, by using constitutively active H3 receptor mutants, screening of drug candidate compounds such as H3 receptor inverse agonists was shown to be possible with more ease and efficiency.

More specifically, the present invention provides the following:

[1] a constitutively active H3 receptor mutant;

[2] the constitutively active mutant of [1], wherein at least one amino acid residue of the activation-regulating site on the C-terminal side of H3 receptor internal domain 3 is substituted with another amino acid residue;

[3] the constitutively active mutant of [1] or [2], wherein an amino acid residue of a site corresponding to at least one of amino acid 352, 353, 354, or 357 in the amino acid sequence of SEQ ID NO: 1 or SEQ ID NO: 3 is substituted with another amino acid residue;

[4] the constitutively active mutant of [1] or [2], wherein the substitution of an amino acid residue in the H3 receptor activation regulating site is either (a) or (b) below:

(a) a substitution from RDRKVAK (SEQ ID NO: 11) to KDHKVLK (SEQ ID NO: 4), RARKVAK (SEQ ID NO: 5), RDRKVIK (SEQ ID NO: 6) or RDRKVKK (SEQ ID NO: 7) in a human H3 receptor; or (b) a substitution from RDKKVAK (SEQ ID NO: 12) to KDHKVLK (SEQ ID NO: 4), RAKKVAK (SEQ ID NO: 8), RDKKVIK (SEQ ID NO: 9) or RDKKVKK (SEQ ID NO: 10) in a mouse, rat, or guinea pig H3 receptor;

[5] the constitutively active mutant of [1] or [2], comprising an amino acid substitution of at least one of (a) to (c) below:

(a) at least a substitution from A to K or I at amino acid 357 in the amino acid sequence of SEQ ID NO: 1;

(b) at least a substitution from D to A at amino acid 353 in the amino acid sequence of SEQ ID NO: 1; and (c) at least a substitution from R to K at amino acid 352, K to H at amino acid 354, and A to L at 357 in the amino acid sequence of SEQ ID NO: 1;

[6] the constitutively active mutant of [1] or [2], comprising an amino acid substitution of at least one of (a) to (c) below:
   (a) at least a substitution from A to K or I at amino acid 357 in the amino acid sequence of SEQ ID NO: 3;
   (b) at least a substitution from D to A at amino acid 353 in the amino acid sequence of SEQ ID NO: 3; and
   (c) at least a substitution from R to K at amino acid 352, K to H at amino acid 354, and A to L at amino acid 357 in the amino acid sequence of SEQ ID NO: 3;

[7] a DNA encoding the constitutively active mutant of any one of [1] to [6];

[8] a vector inserted with the DNA of [7];

[9] a transformed cell comprising the DNA of [7] or the vector of [8];

[10] a method for evaluating whether or not a test compound changes the activity of a constitutively active H3 receptor mutant, wherein the method comprises:
   (a) contacting the test compound with cells expressing the constitutively active H3 receptor mutant; and
   (b) detecting the activity of the constitutively active mutant in the cells,
   wherein the test compound is judged to change the activity of the constitutively active mutant when the activity increases or decreases compared with that in the absence of the test compound;

[11] the method of [10], wherein the activity of the constitutively active mutant is detected by using a change in cAMP concentration, a change in calcium concentration, a change in G protein activity, a change in phospholipase C activity, or a change in pH, as an indicator;

[12] a method of screening for a drug candidate that changes the activity of a constitutively active H3 receptor mutant, wherein the method comprises steps (a) and (b) below:
   (a) using the method of [10] or [11] to evaluate a number of test compounds to determine whether or not they change the activity of a constitutively active H3 receptor mutant; and
   (b) selecting from the number of test compounds a compound(s) judged to change the activity of the constitutively active mutant;

[13] the method of [12], wherein the drug candidate is an H3 receptor inverse agonist.

H3 receptors are known to have constitutively active forms. However, the present inventors produced constitutively active H3 receptor mutants comprising even higher activity than natural constitutively active forms. The present inventors also found that drug candidate compounds can be screened more easily and efficiently by using these constitutively active mutants. The present invention is based on these findings.

The present invention provides constitutively active H3 receptor mutants. Constitutively active H3 receptor mutants in the present invention are preferably substantially purified. In the present invention, "substantially purified" refers to being isolated from the external environment such that other components account for at most 40%, preferably 25%, and more preferably 10% or less. In addition, in the present invention, "constitutive activity" refers to activity in the absence of ligands (i.e., states in which activity exists even when ligands are absent).

The types and number of mutated sites in the constitutively active mutants of the present invention are not particularly limited, however, the mutated sites are preferably located at the activation regulation site on the C-terminal side of H3 receptor internal domain 3. Examples of mutation types include substitution mutations, deletion mutations, and insertion mutations; however, substitution mutations are preferable. Examples of constitutively active mutants comprising this type of mutation are those constitutively active mutants in which at least one amino acid residue at the activation regulation site on the C-terminal side of H3 receptor internal domain 3 is substituted with another amino acid residue. More specifically, examples of constitutively active mutants are those comprising an activation regulation site that includes the sequence KDHKVLK (SEQ ID NO: 4), RARKVAK (SEQ ID NO: 5), RDRKVIK (SEQ ID NO: 6), RDRKVKK (SEQ ID NO: 7), RAKKVAK (SEQ ID NO: 8), RDKKVIK (SEQ ID NO: 9), or RDKKVKK (SEQ ID NO: 10), however, the sequence of the activation regulating site in a constitutively active mutant of the present invention is not limited to these sequences.

In addition, other examples of constitutively active H3 receptor mutants of the present invention include, but are not limited to, constitutively active mutants in which an amino acid residue at a site corresponding to positions 352, 353, 354, or 357 in the amino acid sequence of SEQ ID NO: 1 or SEQ ID NO: 3, is substituted with another amino acid residue. For example, constitutively active mutants in which mutations have occurred at another site are also included in the constitutively active mutants of the present invention, in addition to those described above.

In the present invention, examples of a site that corresponds to positions 352, 353, 354, or 357 in the amino acid sequence of SEQ ID NO: 1 or SEQ ID NO: 3 include positions 352, 353, 354, or 357 in rat H3 receptor (Q9QYN8), similarly to mouse and human H3 receptors.

In addition, constitutively active H3 receptor mutants of the present invention are preferably derived from species including, but not particularly limited to, humans, mice, rats, or guinea pigs.

Human H3 receptors in the present invention refer to H3 receptors comprising an RDRKVAK sequence (SEQ ID NO: 11). Specific examples of human H3 receptors in the present invention include, but are not limited to, Q9Y5N1 of 445AA (SEQ ID NO: 3), BAB20090 of 453AA, and AAK50040 of 365AA. In addition, mouse, rat or guinea pig H3 receptors in the present invention refer to H3 receptors comprising an RDKKVAK sequence (SEQ ID NO: 12). Specific examples of these include, but are not limited to, mouse H3 receptor comprising the amino acid sequence of SEQ ID NO: 1, rat H3 receptors Q9QYN8 of 445AA, BAA88765 of 449AA, BAA88767 of 413AA, and BAA88768 of 397AA, and guinea pig H3 receptor Q9JI35 of 445AA. All H3 receptors comprising the aforementioned specific sequences are reported to comprise similar structural characteristics, activities, and activation regulating site sequences (RDRKVAK (SEQ ID NO: 11) in humans, and RDKKVAK (SEQ ID NO: 12) in mice, rats and guinea pigs).

In addition, the sequences of activation regulating sites of constitutively active human H3 receptor mutants in the present invention preferably comprise, but are not limited to, KDHKVLK (SEQ ID NO: 4), RARKVAK (SEQ ID NO: 5), RDRKVIK (SEQ ID NO: 6) or RDRKVKK (SEQ ID NO: 7). Furthermore, in the present invention, the sequences of activation regulating sites of constitutively active H3 receptor mutants in mice, rats, and guinea pigs are preferably KDHKVLK (SEQ ID NO: 4), RAKKVAK (SEQ ID NO: 8), RDKKVIK (SEQ ID NO: 9) or RDKKVKK (SEQ ID NO: 10), but are not limited to these.

Preferable examples of constitutively active mouse H3 receptor mutants in the present invention include, but are not limited to, constitutively active mutants in which the A of amino acid 357 in the amino acid sequence of SEQ ID NO: 1 is substituted with K or I; constitutively active mutants in which the D of amino acid 353 is substituted with A; or constitutively active mutants in which the R of amino acid 352 is substituted with K, the K of amino acid 354 is substituted with H, and the A of amino acid 357 is substituted with L. For example, there are numerous combinations of the aforementioned substitution mutations.

In addition, preferable examples of constitutively active human H3 receptor mutants include, but are not limited to, constitutively active mutants in which the A of amino acid 357 in the amino acid sequence of SEQ ID NO: 3 is substituted with K or I; constitutively active mutants in which the D of amino acid 353 is substituted with A, or the R of amino acid 352 is substituted with K, the K of amino acid 354 is substituted with H, and the A of amino acid 357 is substituted with L. For example, there are numerous combinations of the aforementioned substitution mutations.

A constitutively active H3 receptor mutant of the present invention can be produced by, for example, introducing a mutation into a DNA that encodes a protein functionally equivalent to a protein that contains the amino acid sequence of SEQ ID NO: 1 or SEQ ID NO: 3, so that the activity of the protein is further increased.

Examples of "a DNA that encodes a protein functionally equivalent to a protein that comprises the amino acid sequence of SEQ ID NO: 1 or SEQ ID NO: 3" include DNAs that encode mutants, alleles, variants or homologues and such of proteins that comprise the amino acid sequence of SEQ ID NO: 1 or SEQ ID NO: 3. Herein, "functionally equivalent" refers to a protein of interest comprising a biological function (role) or biochemical function (property) equivalent to a protein that comprises the amino acid sequence of SEQ ID NO: 1 or SEQ ID NO: 3. In the present invention, examples of biological functions (roles) of a protein that comprises the amino acid sequence of SEQ ID NO: 1 or SEQ ID NO: 3 include intracellular signal transduction functions (e.g., changes in cAMP concentration, calcium concentration, G protein activity, phospholipase C activity, or pH), or functions that control body weight, food intake, and blood insulin or blood leptin levels. In addition, examples of biochemical functions (properties) of a protein that comprises the amino acid sequence of SEQ ID NO: 1 or SEQ ID NO: 3 include the property of binding with histamine or analogs thereof.

Known examples of DNAs that encode such proteins include DNAs derived from humans (PCT/JP99/07280, Lovenberg, T. W. et al., Molecular Pharmacology, 55: 1101-1107, 1999), rats (PCT/JP99/07280, Lovenberg, T. W. et al., Journal of Pharmacology and Experimental Therapeutics, 293: 771-778, 2000), guinea pigs (Tardivel-Lacombe, J. et al., Molecular Neuroscience 11: 755-759, 2000) and mice (WO 2003004637). These sequences have already been disclosed.

In order to prepare DNAs comprising these other sequences, those of ordinary skill in the art can prepare DNAs that encode proteins functionally equivalent to proteins comprising the amino acid sequence of SEQ ID NO: 1 or SEQ ID NO: 3, by introducing suitable mutations into DNAs that encode proteins comprising the amino acid sequence of SEQ ID NO: 1 or SEQ ID NO: 3, using site-directed mutagenesis (Gotoh, T. et al., Gene 152, 271-275, 1995; Zoller, M. J. and Smith, M., Methods Enzymol. 100, 468-500, 1983; Kramer, W. et al., Nucleic Acids Res. 12, 9441-9456, 1984; Kramer, W. and Fritz, H. J., Methods Enzymol. 154, 350-367, 1987; Kunkel, T. A., Proc. Natl. Acad. Sci. USA, 82, 488-492, 1985; Kunkel, Methods Enzymol. 85, 2763-2766, 1988), double primer methods (Zoller, M. J. and Smith, M., Methods Enzymol. 154, 329-350, 1987), cassette mutagenesis (Wells, et al., Gene 34, 315-323, 1985), megaprimer methods (Sarkar, G. and Sommer, S. S., Biotechniques 8, 404-407, 1990) and such. In addition, amino acid mutations can also occur naturally. The number of amino acids that are mutated is normally 30 amino acids or less, preferably 15 amino acids or less, and more preferably five amino acids or less (e.g., three amino acids or less).

Examples of other methods, known to those of ordinary skill in the art, for producing DNAs that encode proteins functionally equivalent to a given protein are methods using hybridization techniques (Sambrook, J. et al., Molecular Cloning 2nd ed., 9.47-9.58, Cold Spring Harbor Lab. Press, 1989). More specifically, those of ordinary skill in the art know techniques for using a DNA sequence that encodes a protein comprising an amino acid sequence of SEQ ID NO: 1 or SEQ ID NO: 3 (e.g., the DNA of SEQ ID NO: 2), or a portion thereof, to isolate DNAs highly homologous to that DNA, and techniques for using these DNAs to isolate proteins functionally equivalent to proteins comprising the amino acid sequence of SEQ ID NO: 1 or SEQ ID NO: 3.

The hybridization conditions for isolating DNAs that encode proteins functionally equivalent to a protein comprising the amino acid sequence of SEQ ID NO: 1 or SEQ ID NO: 3 can be suitably selected by those of ordinary skill in the art. Low stringency conditions are an example of hybridization conditions. Low stringency conditions are, for example, 42° C., 2×SSC and 0.1% SDS during post-hybridization washing, and preferably 50° C., 2×SSC and 0.1% SDS. More preferable hybridization conditions are, for example, high stringency conditions. High stringency conditions are, for example, 65° C., 0.1×SSC and 0.1% SDS. Under these conditions, as temperature increases, DNAs comprising higher homology can be expected to be efficiently obtained. However, a number of elements, such as temperature and salt concentration, are thought to affect hybridization stringency, and those of ordinary skill in the art can achieve similar stringencies by suitably selecting these elements.

In addition, DNAs that encode proteins functionally equivalent to proteins comprising an amino acid sequence of SEQ ID NO: 1 or SEQ ID NO: 3 can be isolated by a gene amplification method such as PCR, using a primer that is synthesized based on the sequence information of a DNA that encodes a protein comprising the amino acid sequence described in SEQ ID NO: 1 or SEQ ID NO: 3 (e.g., the DNA of SEQ ID NO: 2).

Proteins functionally equivalent to proteins comprising the amino acid sequence of SEQ ID NO: 1 or SEQ ID NO: 3, encoded by the DNAs isolated by such hybridization or gene amplification techniques, normally comprise amino acid sequences with high homology to a protein comprising the amino acid sequence of SEQ ID NO: 1 or SEQ ID NO: 3. High homology normally refers to identity of at least 50%, preferably 75% or higher, more preferably 85% or higher, and even more preferably 95% or higher, at the amino acid level.

The degree of identity of one amino acid sequence or nucleotide sequence to another can be determined by Karlin and Altschul's BLAST algorithm (Proc. Natl. Acad. Sci. USA, 90:5873-5877, 1993). Programs such as BLASTN and BLASTX were developed based on this algorithm (Altschul et al., J. Mol. Biol. 215:403-410, 1990). To analyze a nucleotide sequence according to BLASTN, based on BLAST, parameters are set, for example, at score =100 and work length =12. On the other hand, parameters used for the analysis of amino acid sequences by BLASTX, based on BLAST, include, for example, score =50 and word length =3. When using the BLAST and Gapped BLAST programs, each program's default parameters are used. Specific techniques for each analysis are known in the art (ncbi.nlm.nih.gov).

In addition, DNAs that encode proteins functionally equivalent to proteins comprising the amino acid sequence described in SEQ ID NO: 1 or SEQ ID NO: 3 include cDNAs, genomic DNAs and synthetic DNAs. cDNAs can be screened by, for example, using $^{32}P$ or such to label the cDNA described by SEQ ID NO: 2, fragments thereof, their complementary DNAs or RNAs, or synthetic oligonucleotides comprising a portion of the cDNA sequence, and hybridizing these to a tissue-derived cDNA library (e.g., brain, thalamus or hypothalamus) expressing a DNA that encodes a protein functionally equivalent to a protein comprising the amino acid sequence described in SEQ ID NO: 1 or SEQ ID NO: 3. Alternatively, cDNAs can also be cloned by synthesizing oligonucleotides that correspond to the cDNA nucleotide sequence, and amplifying by PCR using a cDNA derived from a suitable tissue (e.g., brain, thalamus or hypothalamus) as a template. Genomic DNAs can be screened by, for example, using $^{32}P$ or the like to label the cDNA described by SEQ ID NO: 2, fragments thereof, their complementary DNAs or RNAs, or synthetic oligonucleotides comprising a portion of the cDNA sequence, and hybridizing these to a genomic DNA library. Alternatively, genomic DNAs can also be cloned by synthesizing oligonucleotides that correspond to the cDNA nucleotide sequence, and amplifying by PCR using genomic DNA as a template. Synthetic DNAs can be prepared by, for example, chemically synthesizing oligonucleotides that comprise a partial sequence of the cDNA of SEQ ID NO: 2, annealing these to form double strands, and then ligating them with DNA ligase (Khorana, H. G. et al., J. Biol. Chem. 251, 565-570, 1976; Goeddel, D. V. et al., Proc. Natl. Acad. Sci. USA 76, 106-110, 1979).

In the present invention, mutations that further increase protein activity are introduced into the DNAs encoding proteins functionally equivalent to proteins comprising an amino acid sequence of SEQ ID NO: 1 or SEQ ID NO: 3 obtained in this manner. The sites at which amino acids are mutated due to the introduction of DNA mutations are preferably sites equivalent to at least one of positions 352, 353, 354, or 357 in the amino acid sequence of SEQ ID NO: 1 or SEQ ID NO: 3, however the sites are not limited to these. In addition, the types of mutations preferably include, but are not limited to, mutations involving amino acid substitution. More specifically, for example, types of mutations include mutations involving amino acid deletion or insertion.

Those of ordinary skill in the art can use known methods to prepare constitutively active H3 receptor mutants from the DNAs that encode the constitutively active H3 receptor mutants obtained in this manner.

In addition, the present invention provides DNAs that encode the aforementioned constitutively active H3 receptor mutants. The DNAs of the present invention have preferably been isolated. Herein, "isolated" refers to the state of having been taken out of an inherent environment and substantially purified.

Such DNAs are useful for producing recombinant proteins. More specifically, constitutively active mutants of the present invention can be prepared by inserting the aforementioned DNAs that encode constitutively active mutants into suitable expression vectors, introducing the vectors into suitable cells, culturing the resulting transformants, and purifying the expressed proteins. In addition, since the constitutively active mutants of the present invention are receptors, they can also be prepared by expression on a cell membrane.

Specifically, if the host is *Escherichia coli*, plasmid vectors such as pET-3 (Rosenburg A. H. et al., Gene 56, 125-135, 1987) and pGEX-1 (Smith D. B. and Johnson K. S., Gene 67, 31-40, 1988) may be used. *E. coli* can be transformed by the Hanahan method (Hanahan D., J. Mol. Biol. 166, 557-580, 1983), electroporation (Dower W. J. et al., Nucleic Acids Res. 16, 6127-6145, 1988), and such. If the host is fission yeast (*Schizosaccharomyces pombe*), a plasmid vector such as pESP-1 (Lu Q. et al., Gene 200, 135-144, 1997) can be used. Yeast can be transformed by spheroplast fusion (Beach D. and Nurse P., Nature 290, 140, 1981), and lithium acetate methods (Okazaki K. et al. Nucleic Acids Res. 18, 6485-6489, 1990), etc.

If the host is a mammalian cell, such as Chinese Hamster ovary-derived CHO cells and human HeLa cells, vectors such as pMSG (Clontech) can be used. Alternatively, in case of HEK293 cells, pcDNA3.1(+) can be used. Recombinant DNAs can be introduced into mammalian cells by the calcium phosphate method (Graham F. L. and van derEb A. J., J. Virology 52, 456-467, 1973), DEAE-dextran methods (Sussman D. J. and Milman G., Mol. Cell. Biol. 4, 1641-1643, 1984), lipofection (Felgner P. L. et al., Proc. Natl. Acad. Sci. USA 84, 7413-7417, 1987), and electroporation (Neumann E. et al., EMBO J. 1, 841-845, 1982), etc. If the host is an insect cell, a baculovirus vector such as pBac-PAK8/9 (Clontech) can be used. Insect cells can be transcribed by methods described in literature (BioTechnology 6, 47-55, 1980).

Recombinant proteins expressed in host cells can be purified by known methods. The proteins can also be synthesized as fusion proteins tagged with histidine residues at the N-terminus, or fused to glutathione-S-transferase (GST), and purified using their binding ability toward a metal-chelating or GST-affinity resin (Smith M. C. et al., J. Biol. Chem. 263, 7211-7215, 1988), respectively. For instance, when the vector pESP-1 is used, the protein of interest can be synthesized as a GST fusion protein, which can then be purified using GST affinity resin. To separate the protein of interest, fusion proteins may be digested with thrombin, or blood coagulating factor Xa.

In addition, the present invention also provides methods for evaluating whether or not a test compound changes the activity of a constitutively active mutant of the present invention. In these methods, a test compound is first contacted with cells expressing a constitutively active mutant of the present invention. There are no particular restrictions as to the test compound used in the present methods, and examples include, but are not limited to, single compounds such as naturally-occurring compounds, organic compounds, inorganic compounds, proteins, peptides or nucleotides, as well as compound libraries, expression products of gene libraries, cell extracts, cell culture supernatants, microbial fermentation products, marine organism extracts, plant extracts, and extracts of tissues or cells for which ligands are predicted to be present (such as the brain, thalamus and hypothalamus).

In addition, cells expressing a constitutively active mutant of the present invention can be produced by, for example, introducing cells (such as HEK293 cells) with a vector containing a DNA encoding a constitutively active mutant of the present invention. The vector can be introduced into the cells by ordinary methods, using calcium phosphate precipitation, electroporation, lipofectamine, microinjection, or such.

In the present invention, "contact" can be carried out by, for example, adding a test compound to a cell culture. When the test compound is a protein, for example, a vector containing a DNA encoding the protein can be introduced into cells expressing a constitutively active mutant.

In the present methods, the activities of the constitutively active mutants in the cells are then detected. The activities of the constitutively active mutants can be detected using intracellular signal transduction (such as changes in cAMP concentration, calcium concentration, G protein activity, phospholipase C activity, or pH) as an indicator. Those of ordinary skill in the art can use known methods to detect the activity of a constitutively active mutant using intracellular signal transduction as an indicator. In the present methods, a test compound is judged to have changed the activity of an aforementioned constitutively active mutant when the activity is increased or decreased compared to that in the absence of test compound contact.

H3 receptor gene knockout mice have been found to demonstrate increased body weight, food intake, and blood insulin or blood leptin levels. Thus, the aforementioned compounds can be drugs for the treatment or prevention of diseases characterized by changes (increases or decreases) in body weight, food intake, and blood insulin or blood leptin levels.

In addition, using the aforementioned evaluation methods, a number of test compounds can be screened for drug candidate compounds that change the activity of a constitutively active mutant. Examples of such drug candidate compounds include, but are not limited to, H3 receptor agonists, antagonists and inverse agonists (inverse agonist drugs that bind to receptors to express an action opposite to agonist pharmacological actions). The agonists and inverse agonists in the present invention include not only those with complete activity, but also those with partial activity. The screening methods of the present invention are more effective methods, especially for screening for various drug candidate compounds that are inverse agonists of H3 receptors.

BRIEF DESCRIPTION OF THE DRAWINGS

FIG. 1 shows the nucleotide sequences of H3 receptors introduced with mutations. m-H3 refers to a wild type mouse H3 receptor.

FIG. 2 shows the amino acid sequences of mouse H3 receptors introduced with mutations.

FIG. 3 shows amino acid sequences of human H3 receptors introduced with mutations. h-H3 refers to a wild type human H3 receptor.

BEST MODE FOR CARRYING OUT THE INVENTION

The present invention will be explained more specifically through the following Examples, but is not limited to these Examples.

EXAMPLE 1

The internal domain 3 of seven transmembrane type G protein-coupled receptors is important for G protein binding or receptor activity, and is well conserved. In H3 receptors, a type of G protein-coupled receptor, this region is also conserved in the same way. An attempt was therefore made to produce constitutively active mouse H3 receptor mutants, and constitutively active human H3 receptor mutants by using PCR to introduce point mutations into a sequence that encodes this region in mouse H3 receptor cDNA and human H3 receptor cDNA.

More specifically, the amino acid mutants were first designed (FIG. 1). Next, PCR was carried out using mouse H3 receptor cDNA (expression vector: pcDNA3.1(+)) as a template, and using primers 722F (5'-AGA ACC CCC ACC TGA TGC-3' (SEQ ID NO: 19)) and 1338R (5'-TCA CTT CCA GCA CTG CTC CAG G-3' (SEQ ID NO: 20)), along with 683F (5'-GCA CTC GTC TTC GGC TGG ATG-3' (SEQ ID NO: 21)) and MT1 (5'-CGA CTT GAG TAC CTT CTT GTC-3' (SEQ ID NO: 22)), MT2 (5'-CGA CTT GAG TAC CTT GTG GTC CTT CGA CAG CCG-3' (SEQ ID NO: 23)), MT3 (5'-CTT CTT GGC CCG CGA CAG CCG-3' (SEQ ID NO: 24)), MT5 (5'-CGA CTT GAT TAC CTT CTT GTC-3' (SEQ ID NO: 25) or MT6 (5'-CGA CTT CTT TAC CTT CTT GTC CCG-3' (SEQ ID NO: 26)). 25 cycles of "94° C. for 15 seconds, 55° C. for 30 seconds, and 72° C. for 30 seconds" were carried out. PCR was conducted again a second time, using the fragments obtained from each PCR reaction as templates, and using primers 683F and 1338R (25 cycles of "94° C. for 15 seconds, 55° C. for 30 seconds, and 72° C. for 30 seconds"). The fragment produced by the second round of PCR (656 bp) was cloned to pCR2.1-TOPO. As a result of inserting point mutations, the BstXI sites of MT1, MT5, and MT6, and the BsmFI sites of MT2 and MT3, were respectively deleted. The introduction of point mutations was then confirmed by sequencing. Next, an Aor51HI-SfiI fragment (174 bp) comprising a point mutation was cloned to mouse H3 receptor cDNA. The Expand High-Fidelity PCR System (Boehringer-Mannheim) was used for all PCR reactions.

Insertion of the point mutation was confirmed by sequencing the mutated DNA fragment. An Aor51HI-SfiI fragment was then cloned to wild type mouse H3 receptor cDNA (expression vector: pcDNA3.1(+)). The aforementioned method was used to produce the MT1, MT2, MT3, MT5, and MT6 clones (FIG. 2).

Wild type mouse H3 receptor cDNA and the five mouse H3 receptor mutant cDNAs were each transfected into cell line HEK293, and screened with G418 to obtain their respective stable clones. Northern analysis was used to check expression levels, and stable clones with roughly equal expression levels were used in the experiment.

Constitutively active human H3 receptor mutants were produced using the same methods (FIG. 3), and mutant-expressing clones were obtained.

EXAMPLE 2

Figure 4:
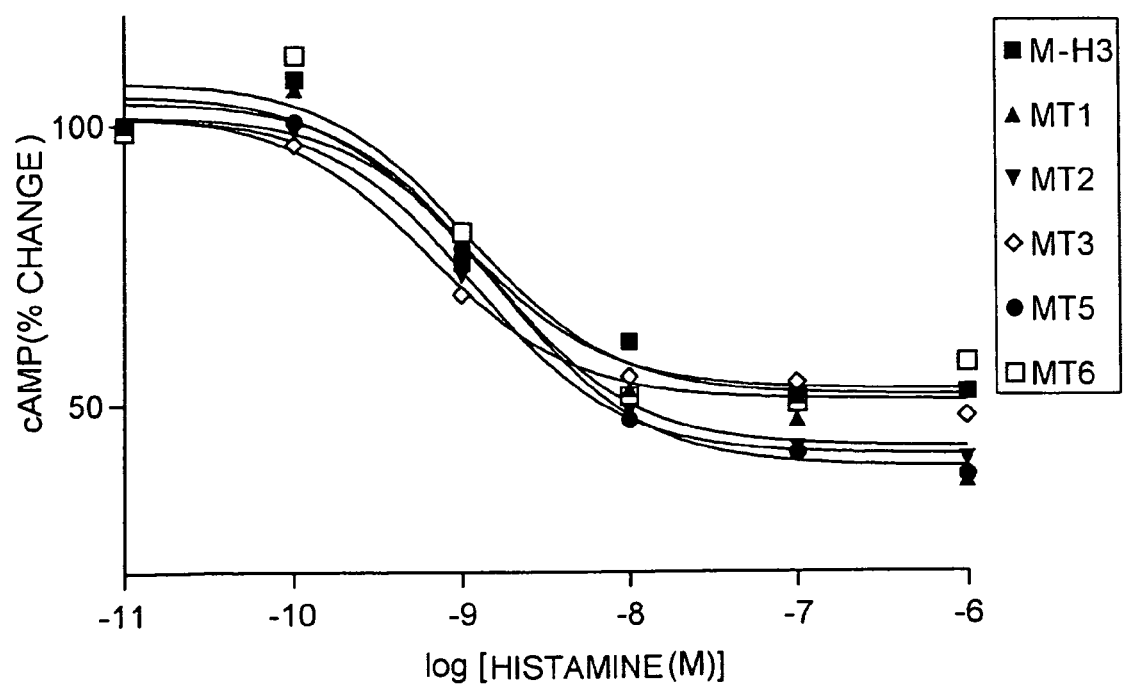
FIG. 4 is shows the histamine-responsiveness of H3 constitutively active mutants.

Since H3 receptors are Gi-binding-type G protein-coupled receptors, cAMP levels were measured using ELISA. More specifically, $10^5$ cells per well were cultured in a 24-well plate the day before testing. On the day of the test, cells were cultured for 15 minutes in the absence of serum, and then treated for 15 minutes with 0.5 mM IBMX. Forskolin (10 μM), histamine ($10^{-11}$ M to $10^{-6}$ M) and thioperamide ($10^{-10}$ M to $10^{-5}$ M) were respectively added, and the cells were treated for 15 minutes. The cAMP Enzyme Immunoassay (EIA) System (Amersham) was used to measure cAMP. The cells were lysed with 150 μl of lysing reagent 1B, provided with the kit. 5 μl of the cell lysate and rabbit anti-cAMP antibody were reacted by being allowed to stand undisturbed at 4° C. for two hours on an antibody-immobilized plate. Moreover, enzyme-labeled antibody was added and reacted by being allowed to stand undisturbed at 4° C. for one hour. The plate was washed with buffer, and enzyme substrate solution was then added and reacted by being allowed to stand undisturbed at room temperature for about 30 minutes. The reaction was stopped with 1 N sulfuric acid, and optical absorbance was then measured. A standard curve was produced from the optical absorbances of standard cAMP solutions, and cAMP levels were determined. A similar test was conducted by treating the cells for 18 hours with pertussis toxin (PTX) at a final concentration of 100 ng/ml. As a result, in the presence of 10 μM forskolin, the cAMP levels in all clones decreased histamine dose-dependently (FIG. 4).

EXAMPLE 3

Figure 5:
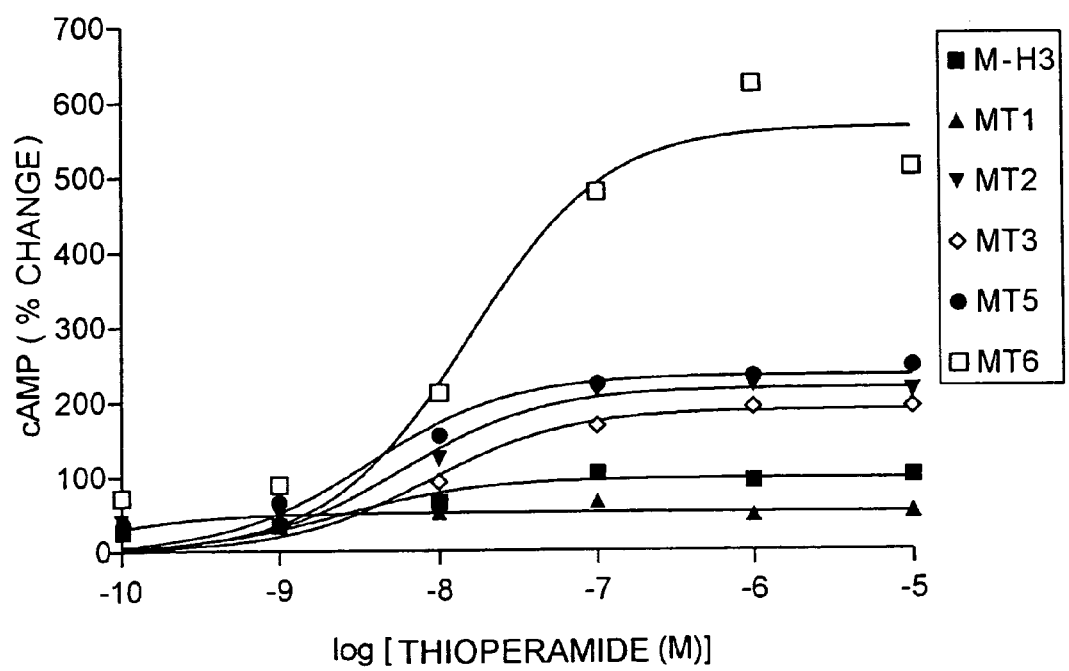
FIG. 5 shows the thioperamide-responsiveness of H3 constitutively active mutants.

In the presence of 10 μM forskolin, the H3 inverse agonist, thioperamide was found to increase cAMP levels dose-dependently, particularly for the MT6 clone (FIG. 5). Although H3 receptors are constitutively active even in their natural states, and are reported to easily adopt constitutively active conformations, the M6 clone was observed to show a cAMP increase of about five-fold compared to the wild type, thus suggesting an extremely strong constitutively active state. In addition, to determine whether the increase in cAMP level caused by thioperamide was mediated by the Gi protein pathway, a similar experiment was conducted by treating the cells with pertussis toxin (PTX) at a final concentration of 100 ng/ml for 18 hours. The results showed that PTX inhibited the increases in cAMP caused by thioperamide were in both the wild type H3 and MT6 clones.

H3 receptors are present in the anterior portion of synapses, and regulate histamine release by functioning as autoreceptors. H3 receptors are constitutively active forms, and act to reduce histamine release, even in the absence of histamine. In addition, histamine acts to further reduce histamine release by binding to H3 receptors.

Histamine acts to reduce appetite when it binds to H1 receptors, present in the posterior portion of synapses. H1 agonists can serve as antiobesity drugs. However, since H1 distribution is ubiquitous, they also comprise actions other than the target action. On the other hand, H3 antagonists and inverse agonists can serve as antiobesity drugs since they increase histamine release by acting only in the central nervous system.

Even constitutively active forms of inverse agonists demonstrate antagonistic effects. In fact, inverse agonists have already been indicated to be more effective than antagonists (Milligan, G. et al., TiPS, 16, 10-13, 1995).

In the present Examples, H3 clones comprising extremely strong constitutive activity were successfully produced by using PCR to introduce point mutations into sequences that encode the internal domain 3 of H3 receptors. The use of these clones is considered to make screening for H3 receptor inverse agonists and such both easier and more efficient.

INDUSTRIAL APPLICABILITY

The present inventors produced constitutively active H3 receptor mutants. By using constitutively active H3 receptor mutants, drug candidate compounds such as H3 receptor inverse agonists can be screened more easily and efficiently.

---

The invention claimed is:

1. A constitutively active mammalian H3 receptor mutant, the mutant comprising at least one mutation in internal domain 3 of the H3 receptor.

2. The constitutively active mutant of claim 1, wherein the internal domain 3 includes an activation-regulating site on its C-terminal side, and the at least one mutation comprises one or more amino acid substitutions within the activation-regulating site.

3. The constitutively active mutant of claim 1, wherein the at least one mutation comprises an amino acid substitution at one or more of positions 352, 353, 354, and 357 in the amino acid sequence of SEQ ID NO: 1 or SEQ ID NO: 3.

4. The constitutively active mutant of claim 1, wherein the at least one mutation includes either (a) or (b) below:
   (a) in a human H3 receptor, replacing RDRKVAK (SEQ ID NO:11) with KDHKVLK (SEQ ID NO:4), RARKVAK (SEQ ID NO:5), RDRKVIK (SEQ ID NO:6) or RDRKVKK (SEQ ID NO:7); or
   (b) in a mouse, rat, or guinea pig H3 receptor, replacing RDKKVAK (SEQ ID NO:12) with KDHKVLK (SEQ ID NO:4), RAKKVAK (SEQ ID NO:8), RDKKVIK (SEQ ID NO:9) or RDKKVKK (SEQ ID NO:10).

5. The constitutively active mutant of claim 1, wherein the at least one mutation comprises at least one of (a) to (c) below:
   (a) a substitution from A to K or I at position 357 in the amino acid sequence of SEQ ID NO: 1;
   (b) a substitution from D to A at position 353 in the amino acid sequence of SEQ ID NO: 1; and
   (c) a substitution from R to K at position 352, K to H at position 354, and A to L at position 357 in the amino acid sequence of SEQ ID NO: 1.

6. The constitutively active mutant of claim 1, wherein the at least one mutation comprises at least one of (a) to (c) below:
   (a) a substitution from A to K or I at position 357 in the amino acid sequence of SEQ ID NO: 3;
   (b) a substitution from D to A at position 353 in the amino acid sequence of SEQ ID NO: 3; and
   (c) a substitution from R to K at position 352, R to H at position 354, and A to L at position 357 in the amino acid sequence of SEQ ID NO: 3.

7. A method for evaluating whether or not a test compound changes the activity of a constitutively active mammalian H3 receptor mutant, wherein the method comprises:

(a) contacting the test compound with cells expressing the constitutively active mammalian H3 receptor mutant of claim 1; and (b) detecting the activity of the constitutively active mutant in the cells, wherein the test compound is judged to change the activity of the constitutively active mutant when the activity increases or decreases in the presence of the test compound compared with activity in the absence of the test compound.

8. The method of claim 7, wherein the activity of the constitutively active mutant is detected by using a change in cAMP concentration, a change in calcium concentration, a change in G protein activity, a change in phospholipase C activity, or a change in pH, as an indicator.

9. A method of screening for a drug candidate that changes the activity of a constitutively active mammalian H3 receptor mutant, wherein the method comprises steps (a) and (b) below:

(a) using the method of claim 8 to evaluate a plurality of test compounds to determine whether or not they change the activity of the constitutively active H3 receptor mutant; and (b) selecting from the plurality of test compounds one or more compounds judged to change the activity of the constitutively active mutant.

10. A method of screening for a drug candidate that changes the activity of a constitutively active H3 receptor mutant, wherein the method comprises steps (a) and (b) below:

(a) using the method of claim 7 to evaluate a plurality of test compounds to determine whether or not they change the activity of the constitutively active H3 receptor mutant; and (b) selecting from the plurality of test compounds one or more compounds judged to change the activity of the constitutively active mutant.

11. The method of claim 10, wherein the drug candidate is an H3 receptor inverse agonist.

12. The method of claim 10, wherein the internal domain 3 includes an activation-regulating site on its C-terminal side, and the at least one mutation comprises one or more amino acid substitutions within the activation-regulating site.

13. The method of claim 12, wherein the at least one mutation comprises an amino acid substitution at one or more of positions 352, 353, 354, and 357 in the amino acid sequence of SEQ ID NO: 1 or SEQ ID NO: 3.

14. The method of claim 12, wherein the at least one mutation comprises either (a) or (b) below:

(a) in a human H3 receptor, replacing RDRKVAK (SEQ ID NO:11) with KDHKVLK (SEQ ID NO:4), RARKVAK (SEQ ID NO:5), RDRKVIK (SEQ ID NO:6), or RDRKVKK (SEQ ID NO:7); or (b) in a mouse, rat, or guinea pig H3 receptor, replacing RDKKVAK (SEQ ID NO:12) with KDHKVLK (SEQ ID NO:4), RAKKVAK (SEQ ID NO:8), RDKKVIK (SEQ ID NO:9) or RDKKVKK (SEQ ID NO:10).

15. The method of claim 12, wherein the at least one mutation comprises at least one of (a), (b) and (c) below:

(a) a substitution from A to K or I at position 357 in the amino acid sequence of SEQ ID NO: 3;

(b) a substitution from D to A at position 353 in the amino acid sequence of SEQ ID NO: 3; and (c) a substitution from R to K at position 352, R to H at position 354, and A to L at position 357 in the amino acid sequence of SEQ ID NO: 3.

16. An isolated DNA encoding a constitutively active mutant of a mammalian H3 receptor, the mutant comprising at least one mutation in internal domain 3 of the H3 receptor.

17. The DNA of claim 16, wherein the constitutively active mutant comprises an amino acid substitution at one or more of positions 352, 353, 354, and 357 in the amino acid sequence of SEQ ID NO: 1 or SEQ ID NO: 3.

18. The DNA of claim 16, wherein the constitutively active mutant has at least one mutation selected from either (a) or (b) below:

(a) in a human H3 receptor, replacing RDRKVAK (SEQ ID NO: 11) with KDHKVLK (SEQ ID NO: 4), RARKVAK (SEQ ID NO: 5), RDRKVIK (SEQ ID NO: 6) or RDRKVKK (SEQ ID NO: 7); or (b) in a mouse, rat, or guinea pig H3 receptor, replacing RDKKVAK (SEQ ID NO: 12) with KDHKVLK (SEQ ID NO: 4), RAKKVAK (SEQ ID NO: 8), RDKKVIK (SEQ ID NO: 9) or RDKKVKK (SEQ ID NO: 10).

19. The DNA of claim 16, wherein the constitutively active mutant has at least one mutation selected from the group consisting of (a) to (c) below:

(a) a substitution from A to K or I at position 357 in the amino acid sequence of SEQ ID NO: 3;

(b) a substitution from D to A at position 353 in the amino acid sequence of SEQ ID NO: 3; and (c) a substitution from R to K at amino acid 352, R to H at position 354, and A to L at position 357 in the amino acid sequence of SEQ ID NO: 3.

20. A vector containing a DNA encoding a constitutively active mutant of a mammalian H3 receptor, the mutant comprising at least one mutation in internal domain 3 of the H3 receptor.

21. A transformed cell comprising (a) a DNA encoding a constitutively active mutant of a mammalian H3 receptor, the mutant comprising at least one mutation in internal domain 3 of the H3 receptor, or (b) a vector containing said DNA.

* * * * *

UNITED STATES PATENT AND TRADEMARK OFFICE
CERTIFICATE OF CORRECTION

PATENT NO. : 7,279,293 B2  Page 1 of 1
APPLICATION NO. : 10/512240
DATED : October 9, 2007
INVENTOR(S) : Kotani et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (98) days Delete the phrase "by 98 days" and insert -- by 91 days --

Signed and Sealed this

Ninth Day of September, 2008

JON W. DUDAS
*Director of the United States Patent and Trademark Office*